(12) United States Patent
Gao et al.

(10) Patent No.: US 11,596,433 B1
(45) Date of Patent: Mar. 7, 2023

(54) INTEGRATED TUMOR RESECTION INSTRUMENT AND SIMULATION TRAINING SYSTEM

(71) Applicants: Yinguang Gao, North Haven, CT (US); Yanhua Xie, North Haven, CT (US); Mitchell Brown, North Haven, CT (US)

(72) Inventors: Yinguang Gao, North Haven, CT (US); Yanhua Xie, North Haven, CT (US); Mitchell Brown, North Haven, CT (US)

( * ) Notice: Subject to any disclaimer, the term of this patent is extended or adjusted under 35 U.S.C. 154(b) by 0 days.

(21) Appl. No.: 17/848,229

(22) Filed: Jun. 23, 2022

(51) Int. Cl.
*A61B 17/3201* (2006.01)
*A61B 90/00* (2016.01)
*G09B 23/30* (2006.01)
*A61B 17/00* (2006.01)

(52) U.S. Cl.
CPC ........ *A61B 17/3201* (2013.01); *A61B 90/361* (2016.02); *G09B 23/30* (2013.01); *A61B 2017/00398* (2013.01); *A61B 2017/00716* (2013.01)

(58) Field of Classification Search
CPC ...... A61B 17/3201; A61B 2017/00716; A61B 2017/00398; A61B 90/361
See application file for complete search history.

(56) References Cited

U.S. PATENT DOCUMENTS

| 2010/0081875 | A1* | 4/2010 | Fowler | A61B 1/041 600/114 |
| 2018/0214171 | A1* | 8/2018 | Ryan, Jr. | A61B 17/3421 |
| 2020/0405403 | A1* | 12/2020 | Shelton, IV | A61B 46/10 |

* cited by examiner

*Primary Examiner* — Vi X Nguyen
(74) *Attorney, Agent, or Firm* — RC Trademark Company (57) ABSTRACT

The invention discloses an integrated tumor resection instrument and a simulation training system. The resection device comprises an imaging system, a minimally invasive incision, a processor, an operating device, a resection executing mechanism and a positioning control device. The operating device is connected to the input end of the processor, the resection actuating mechanism is provided with a resecting driver, and the positioning control device and the resecting driver are both connected to the output end of the processor; the simulation training system comprises the steps of designing a manikin; arranging the imaging system; integrated resection. The resection device can resect the whole tumor along the edge of the tumor, thereby avoiding the incomplete resection and even tumor recurrent caused by crushing in the process of resecting the tumor. The simulation training system can train an operator to quickly master the resection skill and operation of various positions.

5 Claims, 10 Drawing Sheets

INTEGRATED TUMOR RESECTION INSTRUMENT AND SIMULATION TRAINING SYSTEM

TECHNICAL FIELD

The embodiments described herein relate to the field of medical devices, in particular the embodiments relate to an integrated tumor resection instrument and a simulation training system.

BACKGROUND

Traditionally, the complete and integrated resection of a surface tumor requires the skin and subcutaneous tissues to be cut open to expose the subcutaneous mass, and then complete excision is accomplished. Although complete excision of the mass is possible, such an operation leaves a significant surgical scar larger than the diameter of the tumor on the skin after the incision has healed, which has a serious aesthetic impact. The extent of the aesthetic impact of breast surface scars is more pronounced and is more emphasized by patients.

Currently, there are minimally invasive surgery for breast tumors, but the excision method used to remove the tumor is a rotary cut. An ultrasound-guided vacuum-assisted breast biopsy procedure needs to rotate and cut the tumor into small strips of tissue and then the tumor is suctioned out of the body by using negative pressure. It is very easy to cause local shedding of cells and broken tissues during the cutting process, especially in the case of malignant tumors. Moreover, there is a possibility of local tumor implantation after leaving cells or tissues behind. The minimally invasive rotary technique destroys the integrity of the tumor and violates the of "tumor-free" surgical principle.

Therefore, it has become an insurmountable technical barrier to the surgical field to achieve a small incision with no residual tissues or cells left behind and with integrated resection of the tumor.

SUMMARY

The embodiments disclosed herein relate to an integrated tumor resection instrument and an associated simulation training system. The resection device may comprise an imaging system, a processor, an operating device, a resection executing mechanism and a positioning control device. The operating device may be connected to the input end of the processor, the resection actuating mechanism may be provided with a resecting driver, and the positioning control device and the resecting driver may both be connected to the output end of the processor. The resection device may resect the whole tumor along the edge of the tumor, thereby avoiding the incomplete resection and even tumor recurrent caused by crushing in the process of resecting the tumor. The simulation training system may train an operator to quickly master the resection skill and operation of various positions.

BRIEF DESCRIPTION OF THE DRAWINGS

The present invention is described in further detail below in conjunction with the accompanying drawings and specific embodiments.

DETAILED DESCRIPTION

The invention aims to solve the technical problem of providing an integrated tumor resection instrument and a simulation training system. The resection device described herein may be used to resect an entire tumor along its edge, to avoid incomplete resection or even tumor recurrence due to the fragment implantation in the process of tumor resection. The simulation training system may be used to train an operator to quickly master the resection technique and train the operation of various positions. The figures show the following elements: 1 Processor, 2 operating device, 3 resecting actuator, 4 positioning control device, 5 minimally invasive incision, 6 imaging system, 7 tumor simulator, 8 manikin, 9 supporting frame, 10 outer skin, 11 hot melt organic gel, 12 visual interface, 13 organ simulator, 14 ports, 21 angle sensor, 22 tri-axial acceleration sensor I, 23 the shear heads of the scissors, 31 electric telescopic rod, 32 tri-axial acceleration sensor II, 33 guidance mechanism, 34 guidance controller, 35 air conduction tube, 36 the handles of the scissors, 37 the shearing blade, 38 the tail end of the scissors.

In order to achieve the above purpose, the technical solution may comprise an integrated tumor resection instrument, the structure of which includes an imaging system providing a visual interface, a processor for processing control signals, an operating device for issuing action instructions, a resecting actuator for executing action instructions, and a positioning control device for driving the position of the resecting actuator. The operating device may be connected to the input of the processor, the resecting actuator may be provided with a traction rope and a driver, and both the positioning control device and the resecting driver may be connected to the output of the processor. A minimally invasive incision may be used to introduce the resecting actuator into the location of the tumor and to serve as a passage for the removal of the tumor after the integrated resection. The operating device may provide action instructions and may transmit them to the processor according to the outline of the tumor in the visual interface provided by the imagining device and the position of the resecting actuator.

The processor may control the positioning control device and the resecting actuator, and the positioning control device and the resecting actuator together control the resecting actuator to dissect the tumor along its edge.

In one embodiment, the operating device may comprise a simulated scissors, which is mounted with an angle sensor on a rotating shaft of the simulated scissors, and the two shearing heads of the simulated scissors may be mounted with a tri-axial acceleration sensor I.

In some embodiments, a resection executive mechanism is a pair of scissors, the handles of the scissors are made of non-metallic material, and the shear head of the scissors may comprise a magnetic material. A resecting driver may comprise an electric telescopic rod which is hinged between two shear shanks of the scissors. A tail part of each shear shank may be provided with three guiding mechanisms which are controlled by a guiding controller. The guiding controller may be connected to an output of the processor, and the scissors may be inlaid with a tri-axial Accelerometer II, where the wires of the accelerometer II and the electric telescopic rod may be connected to the power supply through a minimally invasive incision.

The positioning control device may include a magnetic field generator which comprises a plurality of flat electromagnets arranged in the front, back, upper, lower, left and right directions of an operation area (e.g., 6 flat electromagnets).

In some embodiments, the guiding mechanism may comprise an airbag, the guiding controller may comprise a two-way air pump, and the airbag and the two-way air pump may be connected through the air conducting tube.

In some embodiments, the guiding mechanism may include a guiding rod, the guiding controller may comprise a stepper motor, and the guiding rod may be connected to a tail of a shear handle by the stepper motor.

In some embodiments, the operating device may comprise an operating table, and the operating table may be provided with a direction control lever and a shear button. In some embodiments, the operating device may comprise an operating table, and the operating table may also include a directional button and a shear button.

A simulated training system for the entire tumor resection using the above-described resection apparatus may comprise the following steps:

In S1, the simulating manikin may be designed where the simulating manikin may include a supporting frame and an outer skin. The interior of the manikin is filled with hot-melt organic colloid, tumor simulator and organ simulator. The organic colloid, tumor simulator and organ simulator may be comprised of sound-permeable materials with different densities. In some embodiments, there may be arrangement ports on the surface of the manikin for situations when the manikin is placed in a water bath so that the hot molten organic colloid is heated up and melted and the tumor simulator is placed in the target position through the arrangement ports. The hot molten organic colloid may be cooled to solidify the hot molten organic colloid and to fix the position of the tumor simulator.

In S2, the imaging system is arranged by initiating the visual interface through the perspective device.

In S3, the integrated tumor resection instrument may be used to dissect the tumor simulator, via the visual interface, from the hot molten organic colloid along the boundary of the tumor simulator where the tumor simulator is not broken and kept intact during the dissecting process. The tumor simulator may be resected entirely and then put into an extraction bag and removed through the minimally invasive incision. In a case that the tumor simulator is too large to pass through the minimally invasive incision directly, the tumor simulator may be shredded in the extraction bag and then removed through the minimally invasive incision, or the minimally invasive incision may be enlarged and then the tumor simulator and/or extraction bag may be removed. In some embodiments, the removal method associated with a tumor/tumor simulator/extraction bag may be negative pressure aspiration. The tumor simulator may be bagged and then pulled out from the incision using a traction rope.

A beneficial effect produced by of the embodiments described herein is that a tumor may be resected entirely along its edge which avoids incomplete dissection or even recurrence of the tumor due to fragmentation implantation during the removal process. In some embodiments, the method described herein introduces magnetic force to control the alignment of the resecting actuator, and combined with a guiding mechanism, a resecting actuator may move synchronously with an and the operating device. The simulation training system has a high degree of simulation and a user can be repeatedly trained and can arrange the tumor simulator in different positions, so that the operator can master the integrated tumor resection at all positions skillfully. Compared to the traditional laparoscopic or robotic surgical device which needs 3-4 ports to operate, the embodiments described herein only require a single port to operate, and do not require intraoperative inflation. The resection executive device described herein is more compact and can perform multi-dimensional operations.

Referring to FIG. 1 through FIG. 6, the integrated tumor resection instrument includes a visual interface 12, provided by imaging system 6, a processor 1 for processing control signals, an operating device 2 for issuing action commands, a resecting actuator 3 for executing action commands, and a positioning control device 4 for driving the position of the resecting actuator 3. The operating device may be in communication with the processor 1. The apparatus and method described herein describe the following elements: a processor 1, an operating device 2, a resecting actuator 3, a positioning control device 4, a minimally invasive incision 5, an imaging system 6, a tumor simulator 7, a manikin 8, a supporting frame 9, an outer skin 10, a hot melt organic gel 11, a visual interface 12, an angle sensor 21, a tri-axial acceleration sensor I 22, an electric telescopic rod 31, a tri-axial acceleration sensor II 32, a guidance mechanism 33, a guidance controller 34 and an air conduction tube 35.

The resecting actuator 3 may be provided with a traction rope and a resecting actuator, and both the positioning control device 4 and the resecting actuator may be communication with the processor 1. The minimally invasive incision may be used to introduce the resecting actuator 3 into the location of the tumor and to serve as a passage for the removal of the tumor after an integrated resection. According to the outline of the tumor in the visual interface provided by the imaging system 6, and the position of the resecting actuator 3, the operating device 2 may provide action instructions and transmits the instructions to the processor 1. The processor 1 may control the positioning control device 4 and the resecting actuator, and the positioning control device 4 and the resecting actuator together control the resecting actuator 3 to dissect the tumor integrated along the its edge.

Figure 1:
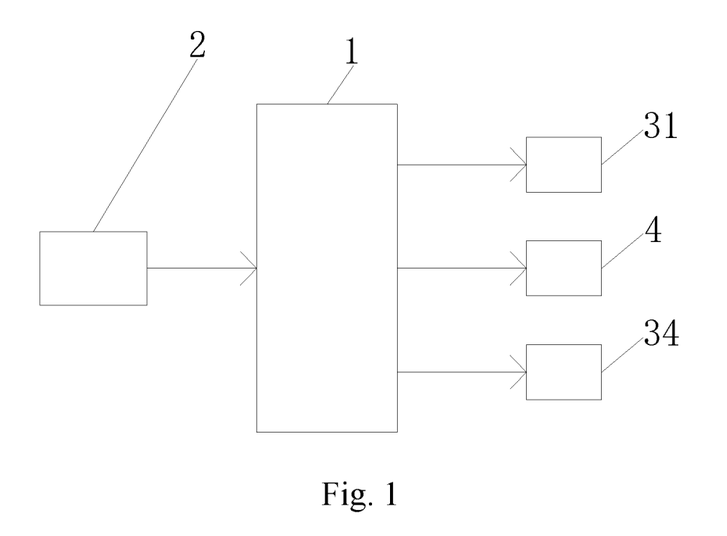
FIG. 1 is a schematic diagram illustrating operation of an integrated tumor resection instrument according to some embodiments.
Figure 2:
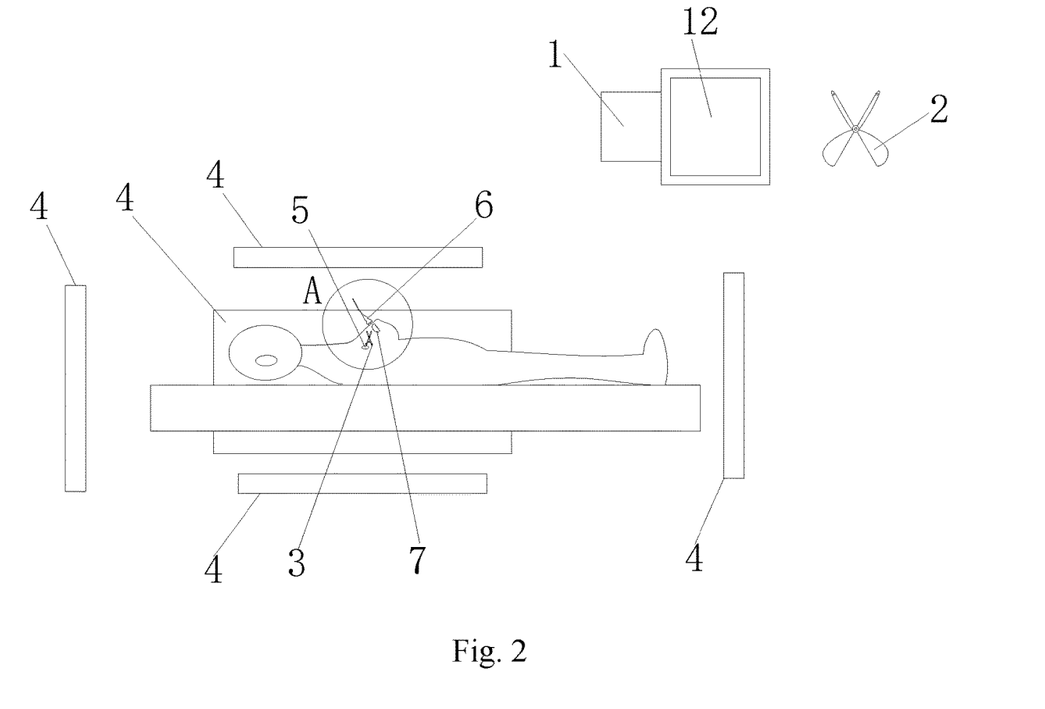
FIG. 2 is a sectional view showing the overall structure of the integrated tumor resection instrument according to some embodiments.
Figure 3:
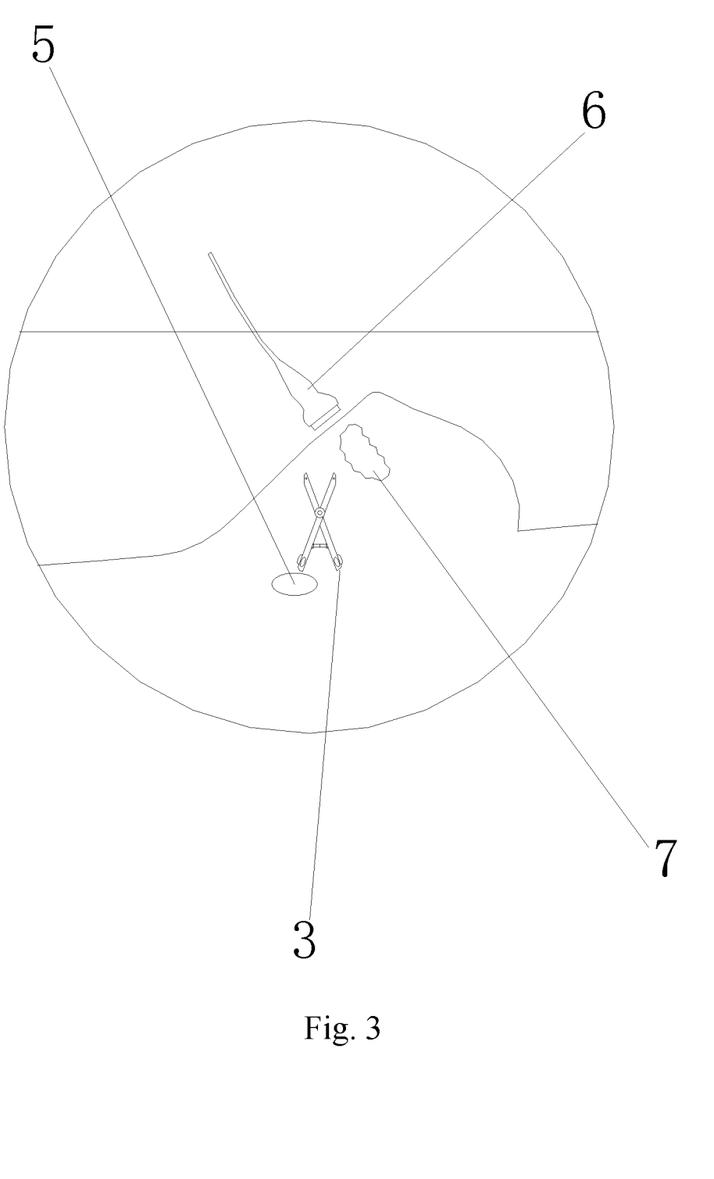
FIG. 3 is a sectional view of a portion of the tumor resection instrument according to some embodiments.

Referring separately to FIG. 3, said operating device 2 is a simulated scissors, which has an angle sensor 21 mounted on the rotating axis of the simulated scissors and a tri-axial acceleration sensor I 22 mounted on the two shear heads 23 of the simulated scissors.

The resecting actuator 3 is a pair of scissors with a non-metallic handle and a magnetic head with shearing blade 37, and the resecting actuator is an electric telescopic rod 31 articulated between the two handles of the scissors 36; three guidance mechanism 33 are provided at the end of each handle 36, and the guides 33 are controlled by a guidance controller 34, which is capable of opening in the outer direction of the handle 36 and in two directions perpendicular to the cutting surface, respectively. The guidance mechanism 33 is controlled by the guidance controller 34, and the three guidance mechanism 33 may be opened in the outer direction of the shear handle 36 and in two directions perpendicular to the shear surface. The guidance controller 34 may be connected to the output end of the processor 1. A tri-axial acceleration sensor II 32 is embedded in the scissors, and wires of the tri-axial acceleration sensor II 32 and the electric telescopic rod 31 penetrate through the minimally invasive incision to be connected to a power supply.

The positioning control device 4 is a magnetic field generator, and the magnetic field generator includes a plurality of flat plate shaped electromagnets (e.g., 6 flat plate electromagnets) set in a plurality of directions such as, but not limited to, in the front, back, top, bottom, left and right of the operation target area (e.g., 6 directions).

Regarding the working principle of the present embodiments, the magnetic field intensity superposition vector algorithm is: the magnetic field generated by any current at a certain point is equal to the vector sum of the magnetic fields generated by all the current elements that make up the current at that point, that is, $$B=\int dB \tag{1}$$

After the dB is expressed by the Biot-Savart Law, and then using the superposition principle, the magnetic field strength generated by any constant current at the target position can be obtained.

The processor 1 may control the strength of the magnetic field of the flat plate shaped electromagnet in each direction of the magnetic field generator through the magnetic field strength superposition vector algorithm to attract the resecting actuator 3 forward, and the attraction is applied at the shearing blade 37 position to increase the forward stability of the scissors. When it is necessary to change direction, the guidance mechanism 33 on the same side of the proposed direction of change opens, and the guidance mechanism 33 pushes the tail end 38 of the resecting actuator 3 to swing in the opposite direction. The open guidance mechanism 33 may enhance the resistance on the same side, thus forcing the resecting actuator 3 to turn in accordance with the operating direction. During the travel of the resecting actuator 3, the electric telescopic rod 31 retracts synchronously with the control command of the operating device 2 to initiate the resecting actuator 3 to perform the shearing action.

The tri-axial acceleration sensor 122 may sense the movement and steering signal of the operating device 2, and the angle sensor 21 may obtain the shearing signal of the operating device 2. After the above signals are processed by the processor 1, the processor 1 may control the magnetic field generator, the resection drive, and the guidance controller 34 to execute the corresponding actions.

Figure 4:
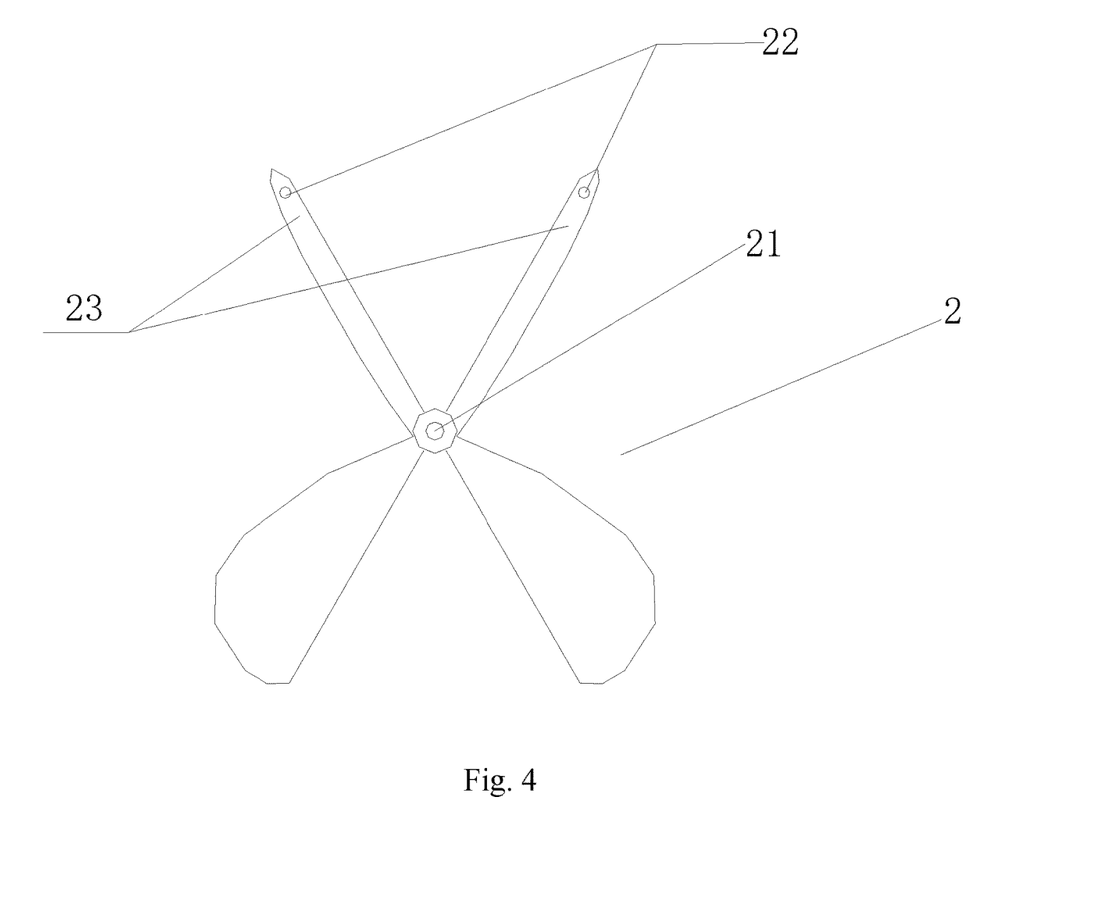
FIG. 4 is a schematic structural diagram of an operating device according to some embodiments.

Referring to FIG. 4, in this embodiment, the guiding mechanism 33 may comprise an airbag, the guiding controller 34 may comprise a bi-directional air pump, and the airbag and bi-directional air pump may be connected through the air conducting tube 35. This embodiment of the airbag may be more rounded than other embodiments, and the opening amplitude may be smaller and suitable for the case of small steering amplitude, such as larger, more round tumors.

Figure 5:
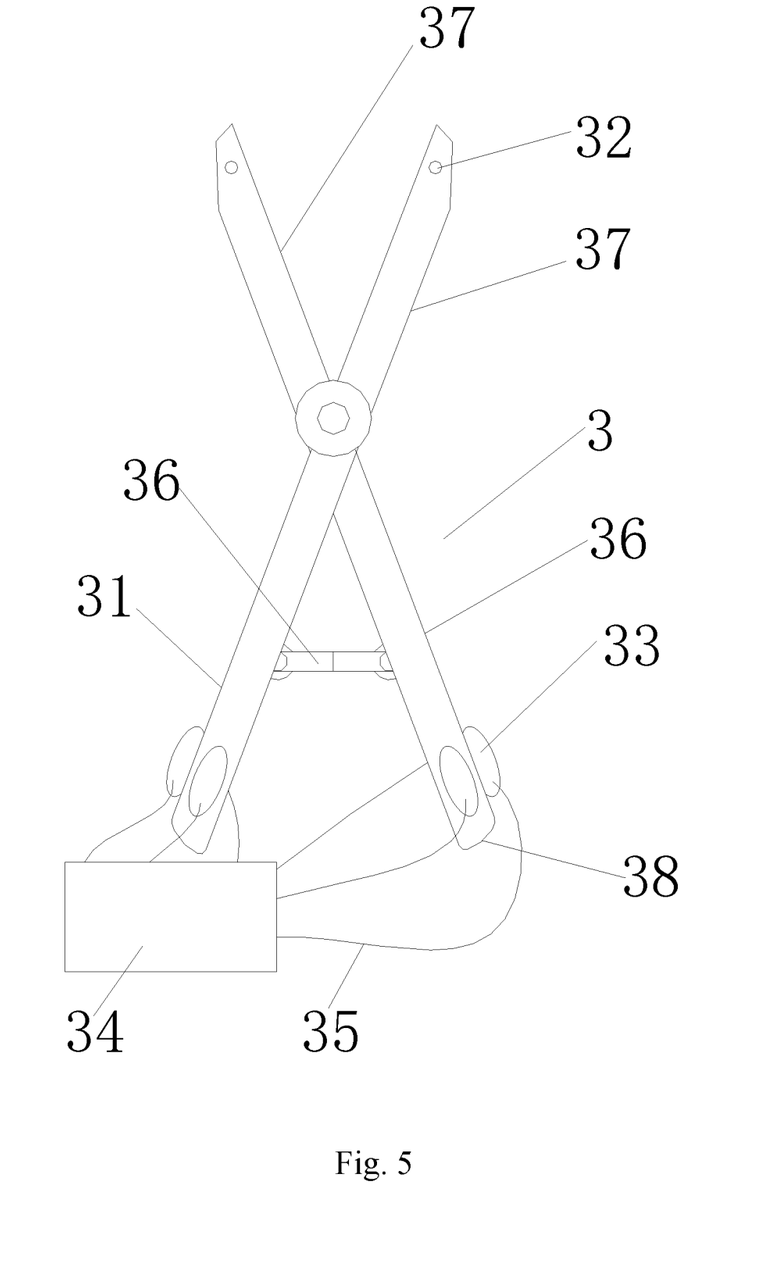
FIG. 5 is a schematic structural diagram of the first representation of the resecting actuator of the integrated tumor resection instrument according to some embodiments.
Figure 6:
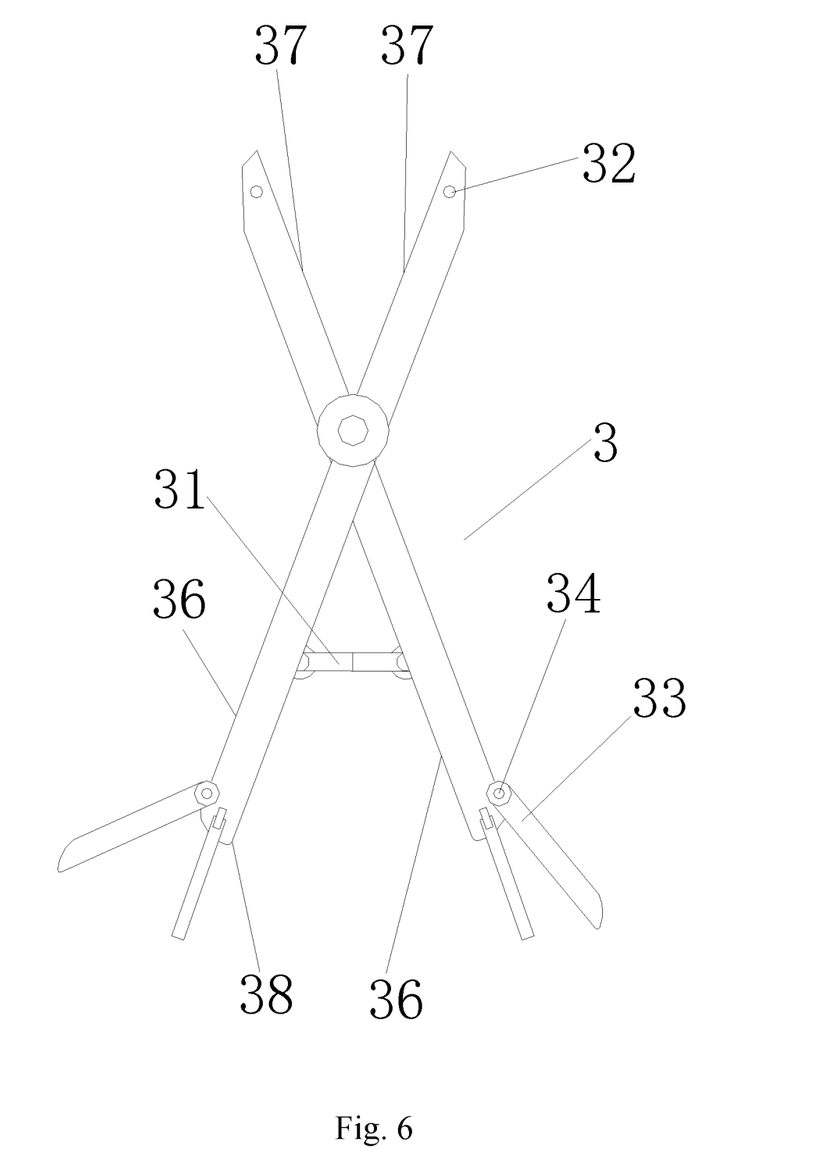
FIG. 6 is a schematic structural diagram of the second representation of the resecting actuator of the integrated tumor resection instrument according to some embodiments.

Referring to FIG. 5, in this embodiment, the guiding mechanism 33 may comprise a guiding rod, and the guiding controller 34 is a stepper motor, and the guiding rod is connected to the tail end of the shear handle by the stepper motor. The outer side of the tail end of the guide bar is a smooth curved surface. The guide bar of this implementation has a high resistance and a large opening amplitude, which may be suitable for situations where the steering amplitude is large, such as smaller, irregular tumors.

In some embodiments, the operating device 2 may comprise an operating table with a directional control lever and a shear button. The lever controls the direction and the shear button may control the shearing action. In some embodiments, the operating device 2 may comprise an operating table with a directional button and a shear button. The direction button may control the direction and the shear button may control the shearing action. The operating device 2 may be capable of being customized to the user's habits, facilitating increased efficiency.

Figure 7:
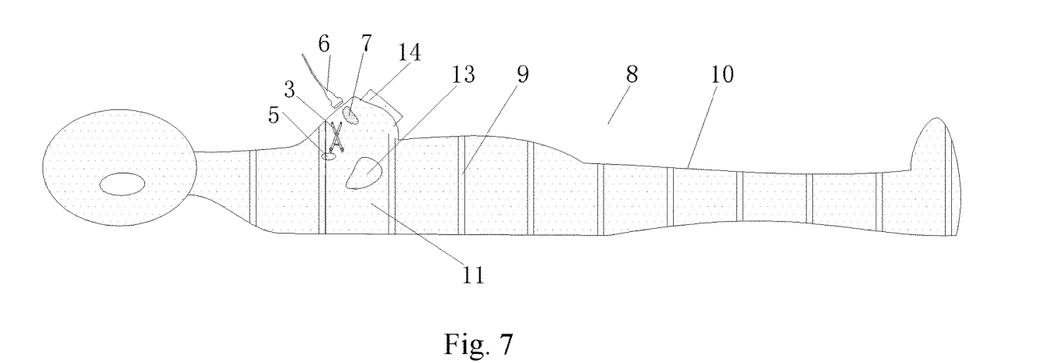
FIG. 7 is a sectional view of the simulated manikin of the simulated training system according to some embodiments.
Figure 8:
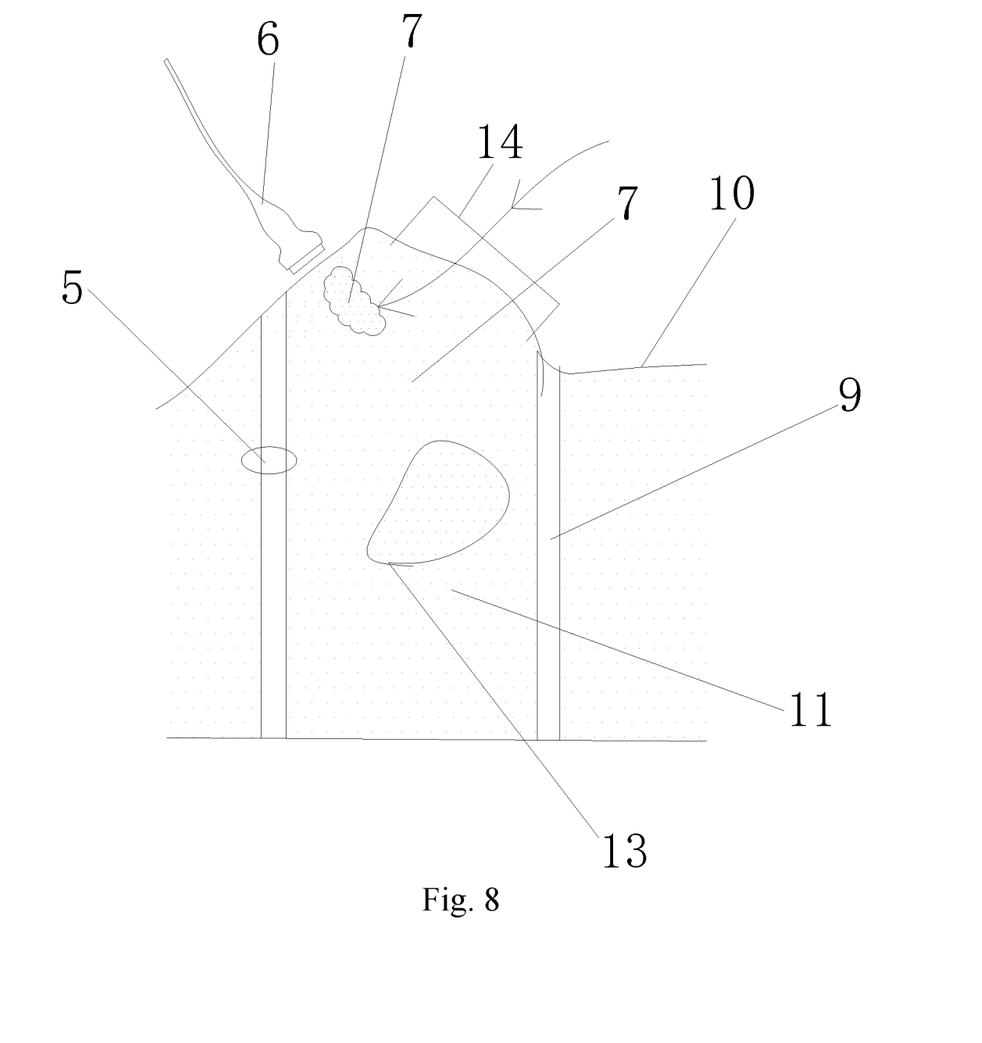
FIG. 8 is sectional view of placing the simulated tumor into the manikin through the port according to some embodiments.
Figure 9:
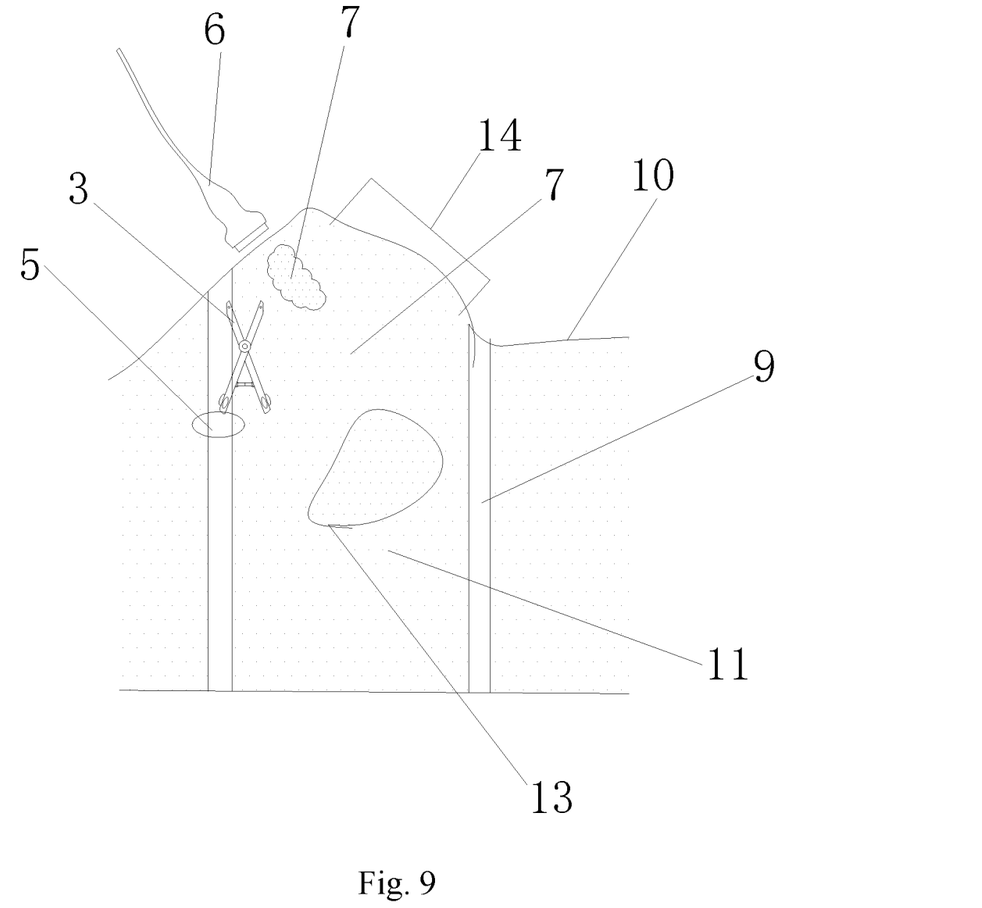
FIG. 9 is a schematic structural diagram of the resecting actuator of the integrated tumor resection instrument according to some embodiments.
Figure 10:
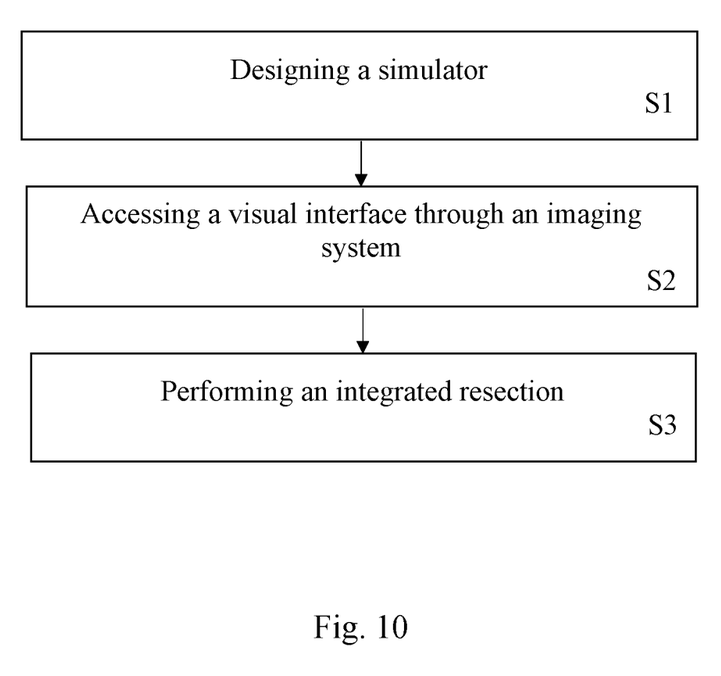
FIG. 10 illustrates a method according to some embodiments.

Referring to FIG. 10, the simulated training system for resecting a tumor as a whole with a resection device may comprise the following steps:

Referring to FIG. 10, at S1, design of simulator: simulator 8 may include a supporting frame 9 and an outer skin 10. The interior of simulator 8 may be filled with a hot molten organic colloid 11, a tumor simulator 7 and organ simulator 13, hot molten organic colloid 11, tumor simulator 7 and an organ simulator 13 which are made of different densities of sound-permeable materials. The hot molten organic colloid 11 simulates human tissue, tumor simulator 7 simulates the lesion of the tissue, organ simulator simulates the importance organs of human body. Simulator 8 may comprise arrangement ports 14 on the surface of simulator 8. The simulator 8 may be placed in a water bath and hot molten organic colloid 11 may be heated up and melted. The tumor simulator 7 may be placed in the target position through the arrangement ports 14. The organ simulator 13 is placed in the corresponding position in the body of the manikin 8 according to the physiological structure, so as to simulate the relationship between the lesion and the important organs. The hot molten organic colloid 11 may be cooled and solidified so that the position of tumor simulator 7 and organ simulator 13 is fixed within simulator 8.

Referring to FIG. 10 (and FIG. 3.) at S2, the visual interface 12 is accessed through the imaging system 6.

At S3, Integrated resection: Under the guidance of the visual interface 12, the resecting actuator 3 is placed near the tumor simulator 7 through the minimally invasive incision 5, and then the operator controls the operating device 2, and the action instructions of the operating device 2 are transmitted to the processor 1. The processor 1 outputs the control command after processing the action command signal. The control command controls the strength of the magnetic field of the flat-shaped electromagnet in each orientation of the positioning control device 4 and then controls the resecting actuator 3 to perform the same action as the operating device 2. The resecting actuator 3 travels along the edge of the tumor simulator 7 resects the tumor simulator 7 out from the hot melted organic colloid 11. Because resection is carried out along the edge of the tumor simulator 7, the tumor simulator 7 will keep intact without being broken.

Due to the high definition of the vision interface of the operating area and the precision operating action, it is possible to avoid any damage to the organ simulant 13 during the operation.

The tumor simulant 7 may be resected and then removed through the minimally invasive incision 5. For a tumor simulant 7 that is too large to pass directly through the minimally invasive incision 5, it may be shredded in a retrieval bag and then removed through the minimally invasive incision 5, or the minimally invasive incision may be enlarged and then the tumor simulant 7 is removed.

There may be two preferred ways to remove the tumor simulator 7 with the first one being negative pressure suction and the second one being pulling out the tumor simulator 7 with a traction line after bagging.

The above description is presented only as an implementable technical solution of the present invention, and not as a single limiting condition on its technical solution itself

What is claimed is:

1. An apparatus for integrally resecting a tumor, the apparatus comprising:
    an imaging system for providing a visual interface for a user;
    a processor for processing a control signal initiated by the user;
    an operating device for sending action instructions via the processor;
    a resection executing mechanism configured for executing the action instruction; and
    a positioning control device configured for controlling movement of the resection executing mechanism by using the imaging device, wherein the operating device is in communication with the processor, wherein the resection executing mechanism is provided with a rope and a resecting driver, wherein the positioning control device and the resecting driver are both in communication with the processor, wherein a minimally invasive incision is used for introducing the resection execution mechanism into a position inside a patient so that a tumor and is removed after the tumor is integrally resected, wherein, and according to the outline of the tumor in the visual interface provided by the imaging device and the position of the resection actuating mechanism, the operating device provides action instructions and transmits the action instructions to the processor, wherein the processor controls the positioning control device and the resecting driver, wherein the positioning control device and the resecting driver jointly control the resection actuating mechanism to dissect the tumor integrally along an edge of the tumor, wherein the operating device is a pair of simulated scissors, wherein an angle sensor is installed on a rotating shaft of the simulated scissors, and wherein a tri-axial acceleration sensor I is installed on two shearing heads of the simulated scissors.

2. The apparatus for integrally resecting tumor of claim 1, wherein the resection actuating mechanism is a pair of scissors, wherein the cutting handles of the scissors are made of nonmetal materials, wherein the cutting heads of the scissors are made of magnetic materials, wherein the resecting driver is an electric adjustable rod which is hinged between the two cutting handles of the scissors, wherein the tail part of each shearing handle is provided with three direction mechanisms which are controlled by a guide controller and can be respectively opened towards the outer side direction of the shearing handle and two directions vertical to the shearing surface, wherein the guide controller is connected to the output end of the processor; wherein a tri-axial acceleration sensor II is embedded in the scissors, wherein the tri-axial acceleration sensor II and a lead of the electric adjustable rod both pass through the minimally invasive incision and are connected to a power supply, and wherein the positioning control device is a magnetic field generator which comprises 6 flat electromagnets which are arranged in the front, the back, the upper, the lower, the left and the right directions of the operation target area.

3. The apparatus for integrally resecting tumor of claim 2, wherein the said direction guiding mechanism is an air bag, the direction controller is a bidirectional air pump, and the air bag is connected with the bidirectional air pump through an air pipe.

4. The apparatus for integrally resecting tumor of claim 2, wherein the guiding mechanism is a guiding rod, the guide controller is a stepping motor, and the guiding rod is connected to the back of the shearing handle through the stepping motor.

5. The apparatus for integrally resecting tumor of claim 1, wherein the operating device is an operating table, and a direction control rod and a shearing button are arranged on the operating table.

* * * * *